(12) United States Patent
Wilde

(10) Patent No.: US 7,493,796 B2
(45) Date of Patent: Feb. 24, 2009

(54) SENSOR FOR DETERMINING A PHYSICAL PROPERTY OF A TEST GAS

(75) Inventor: Juergen Wilde, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 98 days.

(21) Appl. No.: 10/593,583

(22) PCT Filed: Mar. 2, 2005

(86) PCT No.: PCT/EP2005/050920

§ 371 (c)(1),
(2), (4) Date: Jun. 26, 2007

(87) PCT Pub. No.: WO2005/090959

PCT Pub. Date: Sep. 29, 2005

(65) Prior Publication Data

US 2007/0277590 A1   Dec. 6, 2007

(30) Foreign Application Priority Data

Mar. 20, 2004   (DE)   ........................ 10 2004 013 853

(51) Int. Cl.
*G01N 33/00* (2006.01)
*G01N 7/00* (2006.01)
*G01N 27/26* (2006.01)
(52) U.S. Cl. .................. 73/23.31; 73/31.05; 204/428
(58) Field of Classification Search ............... 73/23.31, 73/31.05; 204/428
See application file for complete search history.

(56) References Cited

U.S. PATENT DOCUMENTS

| | | | | |
|---|---|---|---|---|
| 3,835,012 A | * | 9/1974 | Hemak | ........................ 204/428 |
| 4,038,034 A | * | 7/1977 | Nakajima et al. | ............ 422/110 |
| 4,184,934 A | * | 1/1980 | Bode et al. | .................. 204/428 |
| 4,187,163 A | * | 2/1980 | Steinke et al. | ................ 204/428 |
| 4,507,192 A | * | 3/1985 | Ebizawa et al. | ............. 204/428 |
| 4,597,850 A | * | 7/1986 | Takahasi et al. | ............. 204/426 |
| 4,624,770 A | * | 11/1986 | Yamada et al. | ............... 204/428 |
| 4,916,934 A | * | 4/1990 | Nagata et al. | ............... 73/31.05 |
| 4,929,331 A | * | 5/1990 | Kato et al. | .................. 204/426 |
| 5,012,670 A | * | 5/1991 | Kato et al. | .................. 73/31.05 |
| 5,251,470 A | * | 10/1993 | Lampe et al. | ............... 73/31.05 |
| 5,505,073 A | * | 4/1996 | Gerblinger et al. | .......... 73/31.05 |
| 6,342,140 B1 | | 1/2002 | Weyl et al. | |
| 6,637,254 B2 | * | 10/2003 | Wagner et al. | .............. 73/31.05 |

(Continued)

FOREIGN PATENT DOCUMENTS

| | | |
|---|---|---|
| DE | 199 24 319 | 12/2000 |
| EP | 1 046 906 | 10/2000 |
| EP | 1 215 385 | 6/2002 |

*Primary Examiner*—John Fitzgerald
(74) *Attorney, Agent, or Firm*—Kenyon & Kenyon LLP

(57) ABSTRACT

A sensor is described for determining a physical property of a gas that is to be measured, especially the pressure, the temperature or the concentration of a gas component in the exhaust gas of internal combustion engines, which has a sensor element supported in a sensor housing whose gas-sensitive sensor section protrudes from the sensor housing, and has a protective tube that surrounds the sensor section. In order to achieve an effective protection of the gas-sensitive sensor section from water drops and solid substances included in the exhaust gas, in conjunction with cost-effective production of the protective tube, protective tube is developed spiral-shaped, yielding a tube wall that is spiral-shaped in cross section.

13 Claims, 2 Drawing Sheets

U.S. PATENT DOCUMENTS 6,691,553 B2 * 2/2004 Holleboom ................. 73/23.32
6,752,002 B2 * 6/2004 Boltz .......................... 73/23.2

2002/0195339 A1 12/2002 Nakamura et al.

* cited by examiner

SENSOR FOR DETERMINING A PHYSICAL PROPERTY OF A TEST GAS

FIELD OF THE INVENTION

The present invention is based on a sensor for determining a physical property of a test gas, in particular for determining the pressure, the temperature or the concentration of a gas component in the exhaust gas of internal combustion engines.

BACKGROUND INFORMATION

In one known gas sensor for determining the concentration of a gas component, especially oxygen, in exhaust gases of internal combustion engines (German Published Patent Application No. 199 24 319), the protective tube developed as a so-called double protective tube is made up of a measuring chamber, in which the gas-sensitive sensor section lies, surrounded by an inner tube and an outer tube situated concentrically thereto, which enclose a hollow space between them and have gas passage openings for the exhaust gas. In order to avoid that drops of water, carried along distributed in the exhaust gas or created by condensation, deposit on the hot sensor element and trigger the formation of cracks, which leads to the functional failure of the sensor element, flow elements are situated at the gas passage openings which divert the exhaust gas in the direction of the inner lateral surfaces of the inner and outer tube, and thus bind the water drops to the inner lateral surfaces. As a result of the increasing temperature of the exhaust gas, the water subsequently evaporates.

SUMMARY OF THE INVENTION

The sensor according to the present invention has the advantage that, because of the spiral shape of the protective tube, just as in the known sensor element, the access of water drops and solid substances to the sensor element, or, more accurately, to the gas-sensitive sensor section of the sensor element that is enclosed by the protective tube, is reliably prevented without the need for a double tube that is costly from a manufacturing technology point of view. The spiral-shaped protective tube forces the flow, of the gas to be measured, up its spiral-shaped course, because of the centrifugal forces acting upon the gas flow as a result of the flow diversion, the depositing of the water contained therein and the solid substances contained therein being fostered. In addition, because of the spiral-shaped tube wall course of the protective tube, the gas exchange between the exhaust gas flow and the sensor element takes place very much faster, since the spiral diameter, which decreases continuously in the inward direction, speeds up the gas flow. Because of the more rapid gas exchange, the sensor has a greater dynamic measuring range, and detects much more rapidly changes in the gas that is to be measured. The spiral diameter and the number of windings are the parameters influencing the depositing of water and solid substances, and they can be optimized very simply. The smaller, lighter drops and substances precipitate in the region of the smaller spiral diameters, while the heavy drops and substances are deposited on the wall of the tube, already in the region of the greater spiral diameters. The tube wall section of the protective tube, that lies inside, near the sensor element and borders the measuring chamber of the sensor, absorbs the heat radiation of the sensor and heats up very much more rapidly than the outer spiral regions of the protective tube. The exceeding of the dew point is thereby shifted to the cooler outer regions of the protective tube.

According to one advantageous specific embodiment of the present invention, the protective tube is made of sheet metal which, at least on one side, is patterned or coated. Because of this, the depositing of water and substances and their removal by the force of weight, and the pressure gradient in the direction towards the axial exit opening of the protective tube, is supported at the inner wall of the protective tube. Instead of coating the sheet metal, it may also be lined with a nonwoven metal fabric or a ceramic fabric.

According to one advantageous specific embodiment of the present invention, the protective tube is made up of a sintered ceramic, preferably a ceramic foil which is sintered after being formed.

DETAILED DESCRIPTION

Figure 1:
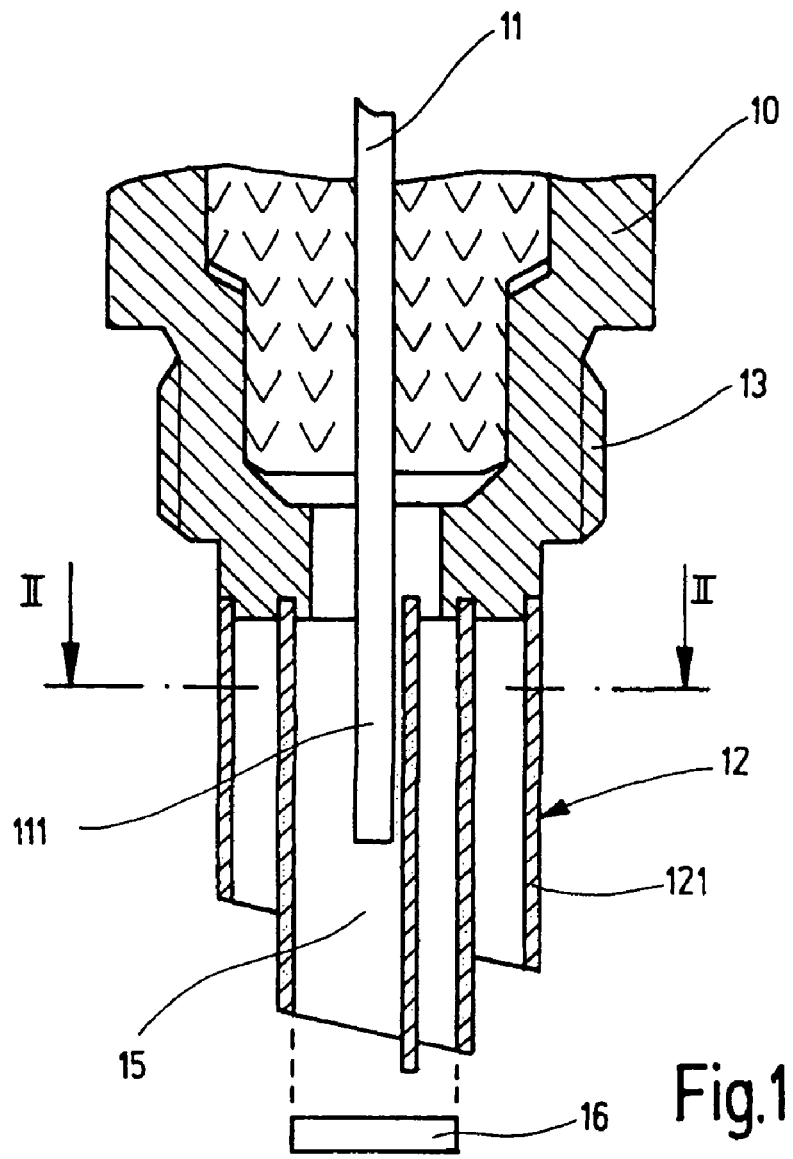
FIG. 1 in a cutaway view, shows a longitudinal section of a gas sensor having a section key according to line I-I in FIG. 2.

The sensor shown in a cutaway view in longitudinal section in FIG. 1, for determining a physical property of a gas to be measured is, for instance, conceived as a lambda probe for determining the oxygen concentration in the exhaust gas of internal combustion engines. The sensor has a sensor housing 10, in which a sensor element 11 is accommodated, which protrudes axially from sensor housing 10 at its gas-sensitive sensor section 111, and is there surrounded by a protective tube which is mounted on the end face of sensor housing 10 and is fastened there. Sensor housing 10 is provided with an outer thread 13 by which the sensor is fastened at the exhaust gas pipe of an internal combustion engine, protective tube 12 extending into the inside of the exhaust pipe, and gas-sensitive sensor section 111 of sensor 11 is exposed to the exhaust gas.

Figure 2:
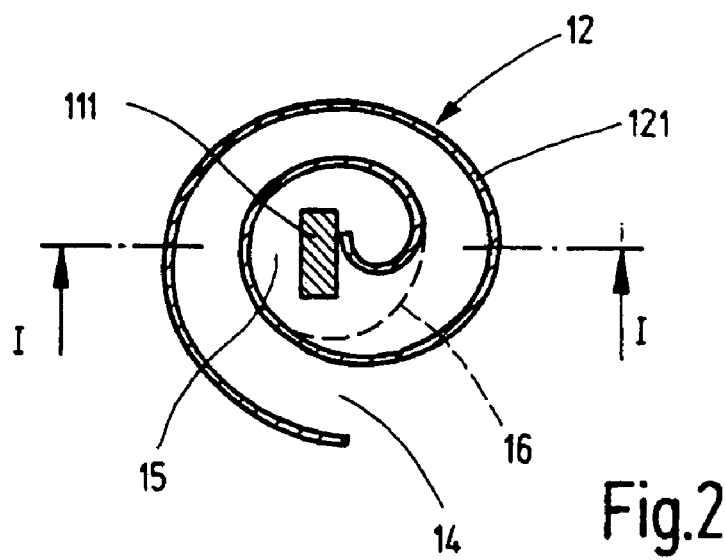
FIG. 2 shows a section along line II-II in FIG. 1.

As may be seen in the sectional representations in FIGS. 1 and 2, protective tube 12 is developed spiral-shaped, that is, its tube wall 121 demonstrates a spiral-shaped course, the spiral diameter of an axially extending inlet opening 14 becoming increasingly smaller, in the direction towards the inside. The innermost spiral region, that is bordered by the tube wall section that directly surrounds sensor element 11, forms a measuring chamber 15 for sensor element 11. Protective tube 12 is open at its end face that faces away from sensor housing 10, so that the exhaust gas entering via inlet opening 14, which is being forced to a spiral-shaped flow within the protective tube spiral, and enters measuring chamber 15, is able to flow out axially via the open end of measuring chamber 15. In the same manner, the water drops and substances depositing on spirally running tube wall 121, which are conveyed to the free end of protective tube 12 by the force of weight and the axial pressure gradient, are able to exit there. For special application purposes, the spiral region enclosing measuring chamber 15 is able to be closed off using a gas-permeable filter 16, as indicated in FIG. 1. Filter 16 is made, for instance, of a porous ceramic fabric or a metal nonwoven wire fabric. Instead of the cover using a filter 16, protective tube 12 may also be developed in such a way that measuring chamber 15 tapers greatly downwards towards the axial exit end, which may be achieved, for example, by squeezing together the free ends of protective tube 12.

Protective tube 12 is preferably made of sheet metal, the sheet metal being patterned at least on one side, for example, sand-blasted, or coated at least on one side. Because of this patterning or coating, the separation of water drops and substances or particles, contained in distributed fashion in the exhaust gas, at spiral-shaped tube wall 121 is substantially aided. For the coating, a ceramic fabric may be used, for example, which is made up, for instance, of 96% aluminum oxide and 4% silicon oxide. Alternatively, protective tube 12 is made up of a sintered ceramic, protective tube 12 being formed preferably from a ceramic foil in a blank state and then sintered. Furthermore, protective tube 12 may be made up of sheet metal and a sintered ceramic. In this context, the sheet metal together with the ceramic foil applied onto it is formed to become protective tube 12, or the sheet metal and the ceramic foil are each formed to a spiral tube separately, and the two spiral tubes are subsequently pushed into each other in the axial direction.

Figure 3:
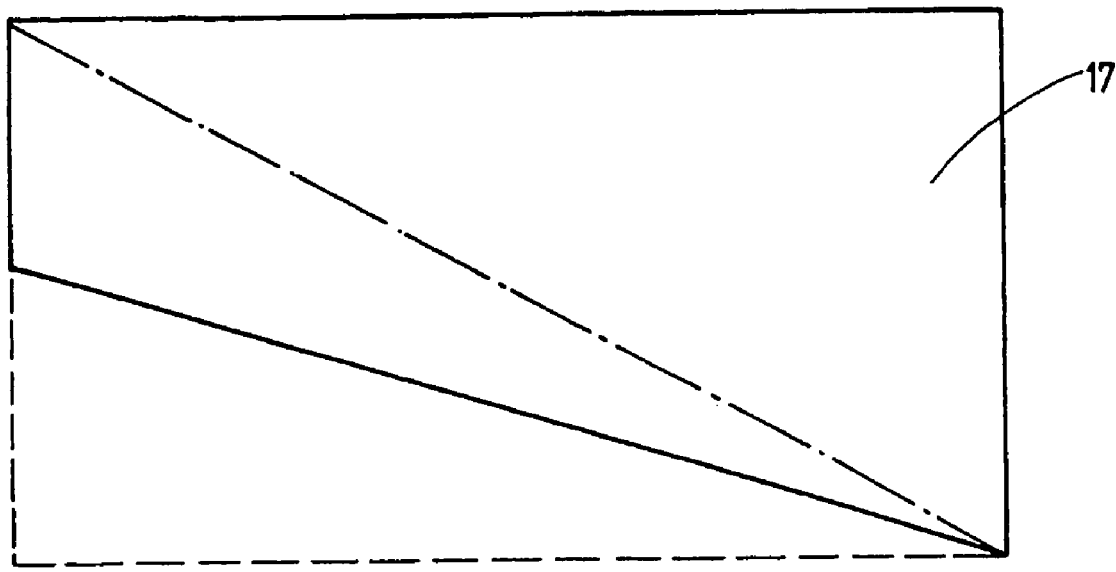
FIG. 3 shows a pattern for a protective tube of the sensor in FIG. 1, according to an additional exemplary embodiment.
Figure 4:
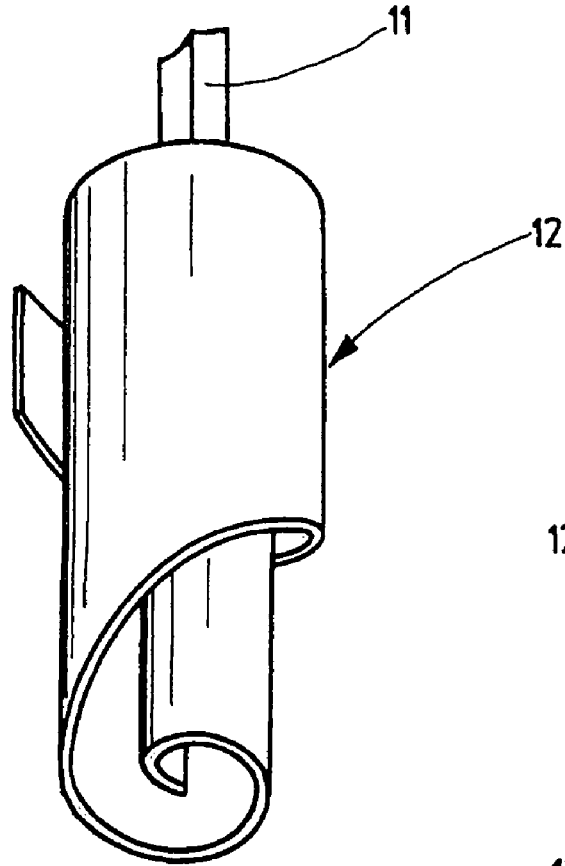
FIG. 4 shows a representation in perspective of a protective tube formed from the pattern according to FIG. 1.

In a preferred manner, protective tube 12 is formed from a flat pattern 17 of sheet metal or a ceramic foil. Such a pattern 17 is shown in exemplary fashion in FIG. 3. Pattern 17 here is a pentagon, in this case. In order to form the spiral tube, pattern 17 is rolled up, starting from its right side, as seen in FIG. 1, and is hardened in its rolled-up state, whereby protective tube 12 comes about, that is shown in perspective in FIG. 4.

Pattern 17 of the sheet metal or the foil, for producing protective tube 12, is able to be designed in various additional geometric shapes, so that correspondingly modified geometric shapes of protective tube 12 come about. Thus, pattern 17 may also be developed in a rectangular or triangular form, as is indicated by dashed and dashed-dotted lines in FIG. 3. The lower longitudinal side edge of pattern 17 may also be given an arch-shaped or curve-shaped course.

Figure 5:
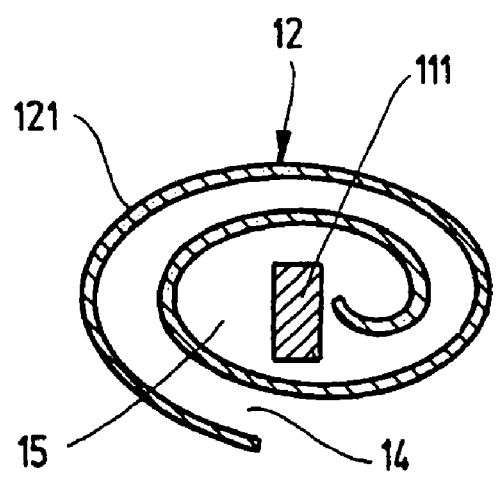
FIG. 5 shows a representation, identical to FIG. 2, of a modified protective tube.

Such a pattern 17 is able to be formed into a spiral-shaped protective tube 12, in which, as may be seen in FIG. 2, the curvature of the tube wall is approximately circular. It is also possible to deviate from the circular form of the curvature of the tube wall and, for instance, roll up pattern 17 in such a way that the tube wall sections include oval interior cross sections, as may be seen in FIG. 5. In such a design of protective tube 12, a directed insertion of the sensor into the gas flow is recommended.

The spiral-shaped protective tube described may also be used, while obtaining the same advantages, for other sensors, such as temperature sensors and pressure measuring sensors for exhaust gas measurements, or for sensors for measuring the concentration of nitrogen oxides in the exhaust gas.

What is claimed is:

1. A sensor for determining a physical property of a gas that is to be measured, comprising:
    a sensor housing;
    a sensor element supported in the sensor housing and including a gas sensitive sensor section that protrudes from the sensor housing; and
    a protective tube that surrounds the sensor section and is fixed at the sensor housing, wherein the protective tube has a spiral-shaped tube wall profile.

2. The sensor as recited in claim 1, wherein the physical property includes one of a pressure, a temperature, and a concentration of a gas component in an exhaust gas of an internal combustion engine.

3. The sensor as recited in claim 1, wherein the protective tube, at least at an innermost spiral region, that is bordered by a tube wall section which directly surrounds the sensor element, is covered at its end face using a gas-permeable filter.

4. The sensor as recited in claim 1, wherein the protective tube, at least at the innermost spiral region, that is bordered by the tube wall section which directly surrounds the sensor element, tapers in a direction of its end face opening.

5. The sensor as recited in claim 1, wherein the protective tube includes a sintered ceramic.

6. The sensor as recited in claim 1, wherein the protective tube includes sheet metal and a sintered ceramic foil applied on top of the sheet metal.

7. The sensor as recited in claim 6, wherein the sheet metal and the ceramic foil are formed together to form the protective tube.

8. The sensor as recited in claim 6, wherein the sheet metal and the ceramic foil are formed each by itself to form a spiral tube, and the two spiral tubes are slipped into each other axially.

9. The sensor as recited in claim 1, wherein the protective tube is produced from sheet metal.

10. The sensor as recited in claim 9, wherein the sheet metal is patterned at least on one side and sand-blasted.

11. The sensor as recited in claim 9, wherein the sheet metal is coated at least on one side.

12. The sensor as recited in claim 9, wherein the protective tube is formed from one of a flat sheet metal pattern and a foil pattern.

13. The sensor as recited in claim 12, wherein the one of the flat sheet metal pattern and the foil pattern includes one of a rectangle, a triangle, and a pentagon.

* * * * *